United States Patent [19]

Müller et al.

[11] Patent Number: 5,648,517

[45] Date of Patent: Jul. 15, 1997

[54] PROCESS FOR THE PREPARATION OF DIALKYL MALEATES

[75] Inventors: Nikolaus Müller, Monheim; Andreas Gröschl, Leverkusen, both of Germany; Ingo Janisch, Groton, Mass.

[73] Assignee: Bayer Aktiengesellschaft, Leverkusen, Germany

[21] Appl. No.: 457,711

[22] Filed: Jun. 2, 1995

[30] Foreign Application Priority Data

Jul. 4, 1994 [DE] Germany .......................... 44 23 355.8

[51] Int. Cl.$^6$ .................................................. C07C 69/52
[52] U.S. Cl. .................................................. 560/205
[58] Field of Search ................................. 560/205

[56] References Cited

U.S. PATENT DOCUMENTS

| | | |
|---|---|---|
| 4,895,989 | 1/1990 | Sander et al. . |
| 4,900,402 | 2/1990 | Kaschemekat et al. . |
| 5,248,427 | 9/1993 | Spiske et al. . |
| 5,360,923 | 11/1994 | Nickel et al. . |
| 5,427,687 | 6/1995 | Blum et al. . |

FOREIGN PATENT DOCUMENTS

| | | |
|---|---|---|
| 0240803 | 10/1987 | European Pat. Off. . |
| 0255399 | 2/1988 | European Pat. Off. . |
| 0255401 | 2/1988 | European Pat. Off. . |
| 0273267 | 7/1988 | European Pat. Off. . |
| 0294827 | 12/1988 | European Pat. Off. . |
| 0299577 | 1/1989 | European Pat. Off. . |
| 0476370 | 3/1992 | European Pat. Off. . |
| 0592883 | 4/1994 | European Pat. Off. . |
| 3114320 | 10/1982 | Germany . |
| 4019170 | 12/1991 | Germany . |

OTHER PUBLICATIONS

H. Lothar, et al., Chemical Abstracts, vol. 105, p. 648, (1986).

R. Rautenbach, et al., Chem.-Ing.-Tech., vol. 61, No. 7, S. 535–544 1989.

U. Sander, et al., Journal of Membrane Science, vol. 61, pp. 113–129, (1991).

*Primary Examiner*—Paul J. Killos
*Attorney, Agent, or Firm*—Sprung Horn Kramer & Woods

[57] ABSTRACT

A process has been found for the preparation of dialkyl maleates from maleic acid, maleic anhydride or monoalkyl maleates with $C_1$–$C_8$-alcohols, in particular ethanol, in the presence or absence of an acidic catalyst and at boiling heat, which is characterized in that the escaping water/alcohol/vapour mixture, together with its condensed phase if appropriate, is conducted as feed along a hydrophilic membrane at which it is purged of water and the dehydrated alcohol is returned to the reaction mixture.

11 Claims, No Drawings

PROCESS FOR THE PREPARATION OF DIALKYL MALEATES

The present invention relates to a process for the preparation of dialkyl maleates, in particular diethyl maleates by esterification of maleic anhydride by alcohols at the boiling temperature of the alcohol component, the resulting vapour mixture of alcohol/water being separated at a membrane and the dehydrated alcohol component being returned to the reaction mixture.

It is already known to prepare dialkyl maleates by esterification of maleic anhydride with excess alcohol (see DE-A 3 114 320, DD-A 229 117). This reaction, as is the case with all esterifications, is an equilibrium reaction which only leads to satisfactory yields if measures are taken to shift the equilibrium. This includes removal of water during the reaction by azeotropic distillation with excess alcohol or an inert entrainer such as toluene. The disadvantage of this process is the consumption of large amounts of alcohol, since lower alcohols are completely miscible with water and can therefore not be returned by phase separation of the distillate. Special dehydration methods must therefore be used for recovery of the alcohol.

When an inert solvent is used as entrainer, separation problems likewise occur in the water/alcohol/entrainer system, so that here also the distillate can not generally be returned directly to the reaction mixture. Both methods of removing water from the circulation lead to prolonged reaction times which, in the case of dialkyl maleates, becomes noticeable in an adverse manner in an intensified isomerization to give fumaric esters (DE-A 3 114 320).

To achieve higher reaction rates, the procedure can be carried out under pressure at temperatures above the boiling point of the-lowest-boiling component. Such higher temperatures generally likewise lead to isomerization and to the formation of other by-products such as alkoxysuccinic esters which can only be removed with great separation effort by distillation (DE-A 3 114 320).

In the preparation of dialkyl maleates, it is additionally important to remove the maleic hemiester formed as an intermediate as completely as possible since separation by distillation of the diester leads to a thermal back reaction of the hemiester with formation of maleic anhydride and alcohol which in turn leads to completely intractable mixtures. The continuous processes described to avoid this disadvantage require high expenditure in terms of equipment with complex recycling operations (EP-A 255 399, EP-A 255 401).

It is further known in the case of chemical equilibrium reactions in which water is formed to separate this off with the aid of semi-permeable membranes and thus to complete the reaction. Such membrane processes for fractionation of mixtures containing organic components are extensively described in the literature (Rautenbach, Chem. Ing. Techn. 61 (1989) pp. 539–544).

Pervaporation and vapour permeation have likewise already been extensively described (DE 3 610 011, DE-A-4 019 170, EP-A 273 267 and EP-A-294 827).

In general in these processes, the mixture to be separated (feed) is conducted along a membrane which has different permeabilities for the individual compounds of the inflowing mixture. The motive force for the mass transport through the membrane is a transmembrane difference in electrochemical potential of the individual substances of the feed mixture. In the case of pervaporation and vapour permeation, this potential difference is imposed by a vacuum applied to the side of the membrane (permeate side) facing away from the feed or by flushing the permeate side with inert gas which causes the feed to be purged of the preferentially permeating component. The depleted feed is termed retentate and the amount of substance passing over the permeate side is termed permeate.

The separation behaviour of membranes is highly temperature-dependent, but is limited by the thermal stability of the membrane used. Thus, for example, the maximum permissible temperature of the membrane Pervap 1000 from GFT of the poly(vinyl alcohol)/polyacrylonitrile type is specified as 100° C.

The processes described in DE-A-3 610 011 and EP-A-240 803 are distinguished in that the feed is fed in in liquid form just below the boiling point at the given system pressure (pervaporation). The system pressure must be chosen in such a way that the temperature of the mixture to be separated at the membrane corresponds as far as is possible to the optimum temperature with respect to permeate flow and selectivity, but must in no case be above the maximum permissible operating temperature of the membrane (membrane stability).

A disadvantage in pervaporation is the temperature drop in the flow direction of the feed caused by the change in phase of the permeating component (evaporation). The evaporation enthalpy of the permeate is removed from the feed mixture so that a temperature decrease occurs in the direction of flow of the feed. As a result of the decrease in temperature, the permeate flow generally greatly decreases, so that to maintain the membrane throughput, the feed mixture must be heated in the meantime EP-A 294 827). This circumstance leads in particular in the case of continuous processes to a complex interconnection of membrane modules and heat exchangers and thus to high capital costs.

Vapour permeation is employed inter alia in EP-A-299 577 in the preparation of alcoholates and is described in the literature "Industrial Application of Vapour Permeation" (U. Sander, I-L Janssen, Journal of Membrane Science, 61 (1991), pp. 113–129). In vapour permeation, in contrast to pervaporation, the feed is conducted over the membrane in the vapour state, i.e. cooling of the feed in the direction of flow occurring during pervaporation as a result of the change in phase from feed to permeate does not occur. In vapour permeation, the complex interconnection of membrane modules and heat exchangers can therefore be dispensed with.

On the other hand, it is a disadvantage in vapour permeation that the permeate flow greatly decreases in the superheated state of the vapour (feed). However, superheating of the vapour cannot be avoided, because of the pressure drops occurring in the direction of flow in industrial modules. The aim therefore always is to operate at the so-called saturated vapour state of the feed, which can be achieved, for example, by compressing the feed between the modules to the extent that the saturated vapour state is achieved on entry to the subsequent module. However, it is a disadvantage in this case that, instead of the heat exchangers required in pervaporation, compressors are necessary to maintain the membrane separation efficiency.

A process has now been found for the preparation of dialkyl maleates from maleic acid, maleic anhydride or monoalkyl maleates with $C_1$–$C_8$-alcohols, in the presence or absence of an acidic catalyst and at boiling heat, which is characterized in that the escaping water/alcohol/vapour mixture, together with its condensed phase if appropriate, is conducted as feed along a hydrophilic membrane at which it is purged of water and the dehydrated alcohol is returned to the reaction mixture.

The alcohol components used in the process according to the invention can be straight-chain or branched, open-chain or cyclic, saturated or unsaturated $C_1$–$C_8$-alcohols. Particular preference is given to those alcohols which form an azeotrope with water and as a result make impossible the separation method by distillation for recycling the alcohol component, such as ethanol, n-propanol and iso-propanol.

The reaction temperatures naturally also depend on the stability of the membrane used. Generally, temperatures of 50° to 150° C., preferably 70° to 130° C., particularly preferably the boiling temperature of the alcohol component are employed.

However, in one of the possible embodiments, these temperatures can be increased or decreased by operating under pressure or vacuum respectively. Elevated temperatures and the accompanying pressure increases can prove to be advantageous, for example, when the alcohol/water vapour mixture has a temperature at atmospheric pressure which is below the optimum working temperature of the membrane used.

The membranes used are described, for example, in EP-592 883 and can be made, for example, of cellulose diacetate, polyimide, cellulose triacetate or poly(vinyl alcohol) or can represent a pore-free layer produced by plasma polymerization. The polymer materials in this case generally have a molecular weight between 15,000 and 200,000. Poly(vinyl alcohol) is generally prepared by extensive saponification of poly(vinyl acetate); the degrees of saponification are to be preferably above 95%, particularly preferably above 98%. Because of the water solubility of poly(vinyl alcohol), this is generally used in crosslinked form. Such crosslinking can comprise etherification, esterification or acetalization by polyfunctional compounds.

In a preferred form, composite membranes are used which generally comprise a plurality of layers, that is a support layer, a porous layer and the actual separation layer. The support layers which are used are generally highly porous flexible cloth or nonwoven webs of fibres, including metal fibres, polyolefins, polysulphones, polyetherimides, poly(phenylsulphides) or carbon; equally suitable are porous structures of glass, ceramics, graphite or metals. The porous reinforcing layer preferably has an asymmetric pore structure. Such porous reinforcing layers can be made, for example, of polysulphone, polyethersulphone, polyetherimide, poly(vinylidene fluoride), hydrolyzed cellulose triacetate, poly(phenylene sulphide), polyacrylonitrile, polyester, polytetrafluoroethylene, polyethylene, poly(vinyl alcohol), copolymers of trifluorinated polyolefins and other suitable polymers. The molecular weights can likewise be in the range from 15,000 to 200,000. The actual separation layer can in turn comprise cellulose diacetate, cellulose triacetate, poly(vinyl alcohol) or a layer produced by plasma polymerization. Poly(vinyl alcohol) is crosslinked in the above-described manner in order to withstand better the attack by water at elevated temperatures. The membranes can be used as a coil-wound module, plate module, pad module, hollow fibre module or capillary module. Coil-wound modules are particularly preferred.

The process is carried out in a preferred embodiment in such a way that the feed is fed to the membrane module as a mixture of vapour and condensed phase, some of the vapour being condensed preferably in a heat exchanger connected upstream of the module, so that the feed has a condensed phase content of 5–90% by weight, preferably 5–50% by weight, in particular 10–20% by weight.

A particularly advantageous dehydration of the feed can be achieved if the feed vapour exiting as retentate from the membrane module is in the saturated vapour state.

The preferably continuous recycling of the dehydrated alcohol (retentate) to the reaction mixture can be carried out either directly as vapour (blowing through) or in the form of the condensed phase, possibly obtained by interposed distillation columns. Vapour phase recycling is preferred.

The acidic catalysts to be used if appropriate can be both inorganic and organic acids, for example sulphuric acid or p-toluenesulphonic acid. The possible amounts of the catalyst are within the ranges conventional for esterification reactions.

The process can moreover be carried out discontinuously or continuously, the continuous mode being able to be carded out in a stirred tank or preferably in a reaction column.

In a further preferred embodiment, the feed (as vapour) is conducted along the membrane under saturated vapour conditions.

The process according to the invention in a preferred embodiment is carried out generally in such a way that in a reaction vessel, molten or solid maleic anhydride is added to previously introduced alcohol, the maleic hemiester forming spontaneously. After addition of the acid catalyst, the mixture is heated until it boils and the alcohol/water mixture distilling off is fed in the vapour state directly or via a short column to the membrane module. A heat exchanger is connected upstream of the module in order to condense some of the vapour and to add the condensed phase to the feed. The permeate is taken off and the retentate is continuously recycled to the reaction mixture. After the reaction is completed, the acidic constituents of the reaction batch (catalyst, monoester) are neutralized by a base and the excess alcohol is distilled off. This can be reused as initial charge in the next batch. The maleic diester is then distilled.

By this process, the diester is obtained in yields of over 95% and in high purities (greater than 99%), i.e. essentially free of isomerization products and addition products.

The processes previously described in the literature for the preparation of dialkyl maleates start from maleic anhydride and the corresponding alcohols, as does a preferred embodiment of the process according to the invention. From the kinetic data for this reaction, which was studied varying the most diverse parameters such as the type and amount of catalyst, molar ratios of starting materials, reaction time and reaction temperature, the results for the reaction with ethanol an equilibrium ratio between monoethylester and diethylester of 24:76. In order to be able to shift this equilibrium, previously either relatively large amounts of ethanol had to be used or the water azetrope had to be removed with the aid of an entrainer. By use of the membrane module in the process according to the invention, conversion into the diethyl ester is surprisingly successively effected quantitatively quite readily in the same reaction time.

The use of the membrane technique in the process described raises the question of the membrane stability, because of the special problems of the maleic anhydride esterification (back formation of volatile maleic anhydride from the hemiester). That is, it was to be expected that entrained hemiester or maleic anhydride would damage the membrane and only give it short service lives which would no longer be economically viable. The use of pervaporation or vapour permeation is associated with the above-described advantages, namely the complex interconnections of membrane modules and heat exchangers or membrane modules and compressors. In particular, in the case of a direct interconnection of distillation and membrane separation unit, increased expenditure is to be expected.

The process described therefore leads in a way which is readily implemented to improved yields of dialkyl maleates without relatively large troublesome amounts of by-products such as fumaric or alkoxysuccinic esters. The reaction times can be considerably shortened. Furthermore, relatively large excesses of alcohol or the use of entrainers can be dispensed with which entrainers need to be recycled in an additional process step after the reaction is completed. The alcohol is preferably used in a molar ratio to each acid function to be esterified of 10:1 to 1:1, preferably 1.1:1 to 1.4:1. The molar ratio of maleic anhydride to alcohol is preferably 1:2.2 to 1:2.5. The amounts of waste water which are formed by neutralization e.g. in the separation of acidic constituents (maleic hemiesters) are likewise considerably decreased by the process according to the invention.

The dialkyl maleates prepared by the process according to the invention serve as precursors for active compounds, wetting agents or paint hardeners.

The process according to the invention may be demonstrated by the following examples.

EXAMPLES

Example 1

467 kg of ethanol are initially introduced into a 1.6 m$^3$ enamelled steel stirred tank having a distillation column, heat exchanger and attached vapour permeation module (54 m$^2$ coil-wound module, poly(vinyl alcohol) of the type Texsep® in FIG. 1 on Ultem® from Texaco) and 328 kg of maleic anhydride and 3.3 kg of p-toluenesulphonic acid are added. The vessel contents are heated to 100° C. bottom temperature and the ethanol/water mixture distilling off is passed via the column in the heat exchanger and into the vapour permeation module. The feed is adjusted here so that the vapour portion is approximately 80 % by weight and the portion of the condensed phase is about 20 % by weight. The permeate (147 kg in 11 hours, of which 61.7 kg are water and 85.3 kg ethanol) is taken off and the retentate (greater than 99% ethanol) is returned in the vapour state to the stirred tank After 11 hours (GC sample), the conversion rate is greater than 95% of theory. After addition of 1 kg of sodium carbonate, the excess ethanol is distilled off via the column and diethylmaleate is produced as main fraction (boiling point 120° C., 20 mbar). The yield is 95% (546 kg, purity at 99%).

Example 2

6.5 kg of isopropanol (IPA) are initially introduced into a 10 l glass vessel having a distillation column, heat exchanger and attached vapour permeation module (0.5 m$^2$ coil-wound module, poly(vinyl alcohol), of the type Texsep® 4 from Texaco) and 3.5 kg of maleic anhydride and 0.04 kg of sulphuric acid are added. The vessel contents are heated to 100° C. bottom temperature and the IPA/water mixture distilling off is passed via the column in the heat exchanger and into the vapour permeation module. The feed is adjusted here so that the vapour portion is approximately 80% by weight and the portion of condensed phase is about 20% by weight. The permeate (0.7 kg in 5 hours, of which 0.67 kg is water and 0.3 kg IPA) is taken off and the retentate (greater than 99% IPA) is returned to the stirred tank. After 10 hours (GC sample), the conversion rate is greater than 95% of theory. After addition of 0.1 kg of sodium hydrogen carbonate, the excess IPA is distilled off via the column and diisopropyl maleate is produced as the main fraction. The yield is 95% (6.8 kg purity at 99%).

We claim:

1. Process for the preparation of dialkyl maleates from maleic acid, maleic anhydride or monoalkyl maleates by reaction with $C_1$–$C_8$-alcohols in the presence of an acidic catalyst and at boiling heat, wherein the escaping water/alcohol/vapour mixture, together with its condensed phase, said condensed phase comprising 5–90% by weight of the total mixture, is conducted as feed along a hydrophilic membrane at which it is purged of water and the dehydrated alcohol is returned to the reaction mixture.

2. Process according to claim 1, wherein the $C_1$–$C_8$-alcohols used are those which form an azeotrope with water.

3. Process according to claim 1, wherein the $C_1$–$C_8$-alcohol used is ethanol.

4. Process according to claim 1, wherein maleic anhydride and ethanol are used as starting materials.

5. Process according to claim 1, wherein the membrane used has been produced from cellulose diacetate, cellulose triacetate, poly(vinyl alcohol) or polyamide or represents a pore-free layer produced by plasma polymerization.

6. Process according to claim 1, wherein the membrane used is a composite membrane.

7. Process according to claim 1, wherein the membrane is used in the form of a coil-wound module.

8. Process according to claim 1, wherein the molar ratio of alcohol to each of the esterifying acid functions is 10:1 to 1:1.

9. Process according to claim 1, wherein the molar ratio of alcohol to each of the esterifying acid functions is 1.1:1 to 1.4:1.

10. Process according to claim 1, wherein the portion of the condensed phase in the feed is 5–50% by weight.

11. Process according to claim 1, wherein the portion of the condensed phase in the feed is 10–20% by weight.

* * * * *